United States Patent [19]

Sturm et al.

[11] 4,161,533

[45] Jul. 17, 1979

[54] 5-SULFAMOYL-ORTHANILIC ACIDS AND PROCESS FOR THEIR PREPARATION

[75] Inventors: Karl Sturm, Heidesheim; Roman Muschaweck, Frankfurt am Main, both of Fed. Rep. of Germany

[73] Assignee: Hoechst Aktiengesellschaft, Frankfurt am Main, Fed. Rep. of Germany

[21] Appl. No.: 900,135

[22] Filed: Apr. 26, 1978

[30] Foreign Application Priority Data

Apr. 28, 1977 [DE] Fed. Rep. of Germany ....... 2718871

[51] Int. Cl.$^2$ .................. A61K 31/34; A61K 31/38; C07D 307/52; C07D 333/20
[52] U.S. Cl. .................................. 424/285; 424/275; 260/239.6; 260/239.65
[58] Field of Search ................ 260/239.6, 239.65; 424/275, 285

[56] References Cited

U.S. PATENT DOCUMENTS

| | | | |
|---|---|---|---|
| 3,356,692 | 12/1967 | Horstmann et al. | 260/347.2 |
| 3,454,562 | 7/1969 | Loev et al. | 260/239.6 |
| 3,875,150 | 4/1975 | Feit et al. | 260/239.6 |

FOREIGN PATENT DOCUMENTS

| | | | |
|---|---|---|---|
| 1192656 | 5/1965 | Fed. Rep. of Germany | 260/347.2 |
| 1278443 | 9/1968 | Fed. Rep. of Germany | 260/397.7 |
| 1802208 | 5/1970 | Fed. Rep. of Germany | 260/239.6 |
| 2247828 | 5/1974 | Fed. Rep. of Germany | 260/239.6 |

OTHER PUBLICATIONS

Crossley et al., J. Am. Chem. Soc., vol. 60, pp. 2217 to 2222 (1938).

*Primary Examiner*—John D. Randolph
*Attorney, Agent, or Firm*—Curtis, Morris & Safford

[57] ABSTRACT

Salidiuretically-active 5-Sulfamoyl-orthanilic acids and their salts, substituted in 4-position by halogen, methyl, phenoxy or phenylthio and by furyl or thienyl at the nitrogen atom, are disclosed, as is and a process for their manufacture by reacting a furyl- or thienyl-substituted amine with corresponding halogen-substituted benzene derivatives.

9 Claims, No Drawings

5-SULFAMOYL-ORTHANILIC ACIDS AND PROCESS FOR THEIR PREPARATION

The invention relates to 5-sulfamoyl-orthanilic acids, and their salts, which have a diuretic and saluretic action and are of the general formula I

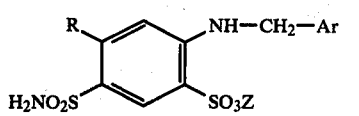

wherein R denotes a chlorine or bromine atom, a methyl group or a phenoxy or phenylthio radical which is optionally substituted by a chlorine or bromine atom or a methyl or methoxy radical, Ar denotes a furyl or thienyl radical and Z denotes a hydrogen atom or a physiologically acceptable metal ion, ammonium ion or substituted ammonium ion, preferably an alkali metal ion.

The invention also relates to a process for the preparation of compounds of the general formula I, which comprises reacting an amine of the general formula II

wherein Ar has the abovementioned meaning, either (a) with a phenylbenzenesulfonate of the general formula III

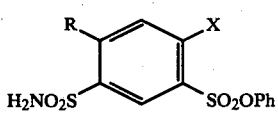

wherein R has the above meaning, X denotes a halogen atom, but denotes a fluorine atom if R represents Cl or Br, Ph denotes an optionally substituted aromatic radical and the sulfonamide group is optionally protected by a radical which is easily detachable by hydrolysis, and subsequently subjecting the resulting compound of the general formula IV

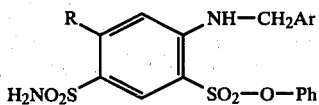

to alkaline saponification, or (b) with benzenesulfonic acids of the general formula V

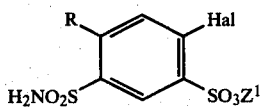

wherein Hal denotes a halogen atom, $Z^1$ denotes a hydrogen, metal, ammonium or tertiary ammonium ion, R has the above meaning and the sulfonamide group is optionally protected by a radical which is easily detachable by hydrolysis, detaching the sulfonamide protective group by hydrolysis if appropriate and optionally converting the compounds obtained according to (a) and (b) into the free acids or other physiologically acceptable salts.

When the products are prepared according to variant (a), an amine of the general formula II is reacted, in the first stage, with a sulfonic acid ester of the general formula III to give a compound of the general formula IV.

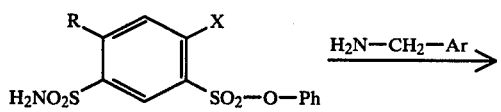

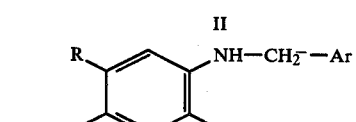

Substances which can be used as the phenolic component of the sulfonic acid ester grouping in III are, in addition to phenol, preferably substituted phenols, such as, for example, o-, m- and p-cresol, 4-chlorophenol, 4-nitrophenol, 4-hydroxyanisole, 4-hydroxyphenetole, 3,5-dimethylphenol, 3,4-dimethylphenol and 3,5-dichlorophenol and it must be taken into account that the rate of saponification of the sulfonic acid ester group is increased by electron-attracting substituents ($NO_2$) in the phenol part and reduced by electron donors ($OCH_3$) and orthosubstituents in the phenol part.

For example, the unsubstituted phenyl ester and the cresyl esters, which as a rule crystallize even better, are very particularly suitable. In place of the above-mentioned substituted phenols, higher-molecular aromatic hydroxy compounds, such as, for example, 1- or 2-naphthol, 2-hydroxycarbazole, 4-hydroxydiphenyl or 6-hydroxyquinoline, can also be used.

The replaceable halogen atom X is preferably F or Cl. The fluorine compounds result in virtually quantitative yields when they are reacted with the amine of the general formula II, but they require a relatively high expenditure on synthesis. It is therefore industrially more advantageous to use the chlorine compounds as the starting material.

Before the condensation reaction with the base, the sulfonamide group in the compounds of the general formula III can be substituted by a radical which is easily detachable by hydrolysis. Reactions suitable for this purpose are, above all, the condensation reaction with formamide acetals to give aminomethylidenesulfonamides

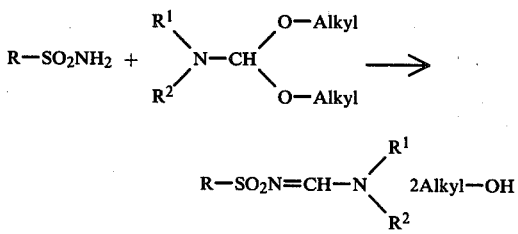

and the reaction with carboxylic acid chlorides or carboxylic acid anhydrides to give the corresponding monoacyl-sulfonamides. The reaction with dimethylformamide dimethylacetal in dimethylformamide at 40°–80° C. to give III a and the reaction with acetic anhydride in pyridine to give III b are preferred.

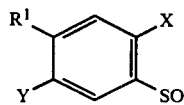

Y = SO₂N=CH—N(CH₃)₂  IIIa
Y = SO₂NH—COCH₃      IIIb

The abovementioned derivatives are split easily during the subsequent alkaline saponification, the unsubstituted sulfonamide being formed again.

The starting materials of the general formula III wherein R denotes an optionally substituted phenoxy or phenylthio radical, but not a methyl group, can be prepared, for example, in accordance with the equation given below (compare (Example 1):

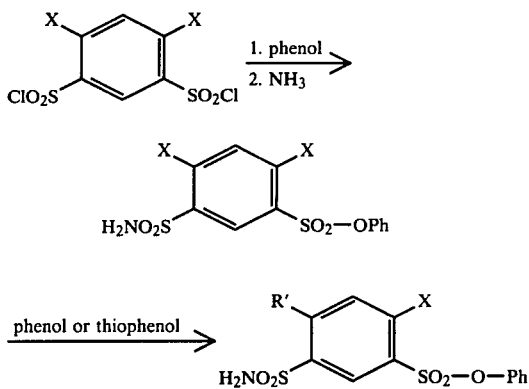

(R′ = (substituted) phenoxy or phenylthio radical).

The compounds III in which R=CH₃ are advantageously synthesized in accordance with the equation given below (compare Example 5):

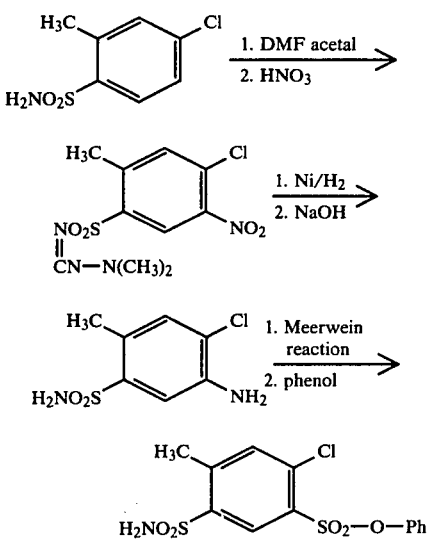

When the reaction is carried out with III, at least 1 mole equivalent of the base of the formula II, preferably furfurylamine or 2-thenylamine, is used and an acid-binding agent, such as, for example, pyridine, triethylamine, dimethylaniline, sodium carbonate or potassium carbonate, is optionally used. Advantageously, either 2 to 3 mole equivalents of the base II are used and a water-miscible inert diluent, such as, for example, dimethylformamide, dimethylacetamide, diethylene glycol dimethyl ether, dioxane, hexamethylphosphoric acid triamide or tetramethylurea, is added, or more than 3 mole equivalents of II are used and the reaction is carried out without the addition of a diluent.

The reaction temperatures are between 20° and 100° C. when X=F and between 60° and 120° C. when X=Cl.

For working up, the reaction mixture is introduced into dilute aqueous acids, preferably acetic acid, whereupon, in many cases, the end product already separates out as crystals and can be purified by recrystallization from methanol, ethanol, isopropanol or mixtures of these alcohols with water. Amorphous crude products are advantageously taken up in a suitable organic solvent, advantageously ethyl acetate, and the dried solution is concentrated and the end product is precipitated as crystals by adding a non-solvent, such as, for example, diisopropyl ether, diethyl ether or petroleum ether, in portions, or the dried solution is evaporated completely and the residue is recrystallized from another organic solvent, such as, for example, toluene, xylene, nitromethane, cyclohexane or acetonitrile. Products which cannot be made to crystallize by these methods are advantageously chromatographed on a silica gel column.

The subsequent alkaline saponification of the intermediates of the general formula IV to give the end products of the general formula I is carried out with inorganic bases, advantageously with excess aqueous 1 N to 5 N sodium hydroxide solution and potassium hydroxide solution. The rate of saponification is influenced both by the radical Ph and by the radical R, so that the reaction times can vary between 1 and 10 hours. In the case of higher-molecular radicals R and Ph it can be advantageous to add diethylene glycol dimethyl ether or dioxane to the mixture in order to obtain a homogeneous solution when hot.

According to process variant (b), a sulfonic acid of the general formula V, or a corresponding salt of this sulfonic acid, is reacted with at least one mole equivalent of an amine of the general formula II, optionally with the addition of an acid-binding agent, and the process products of the general formula I are obtained direct.

In the case of process variant (b) also, it is possible, in principle, to protect the sulfonamide group, as described above under (a), by a radical which is easily detachable by hydrolysis and to detach this radical again, after the amine condensation reaction, by warming in aqueous alkaline solution.

Analogously to procedure (a), the reaction can be carried out with or without a solvent. The reaction temperatures are between 20° and 130° C. when X=F and between 50° and 160° C. when X=Cl and Br. The end products are isolated in a conventional manner by diluting with water, neutralizing and, if necessary, concentrating the reaction mixture, and the compounds of the formula I crystallize out as sulfonic acid salts of the amines II employed.

The preparation of the starting materials of the general formula V in which R=Cl or Br can be carried out, for example, in accordance with or analogously to the equation given below (compare Example 8):

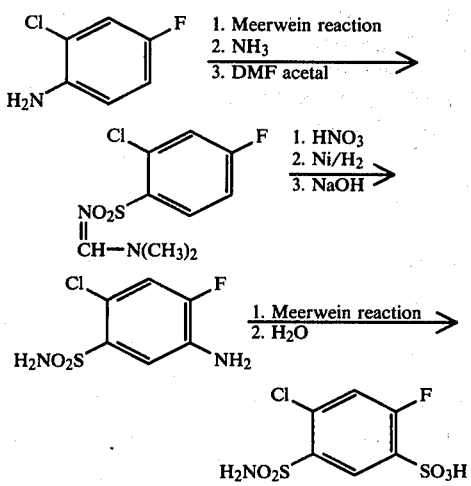

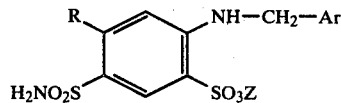

Starting materials of the general formula V in which R denotes a (substituted) phenoxy racial or $CH_3$ can be obtained in a simple manner by alkaline saponification of the sulfonic acid esters of the general formula III, described above.

In the form of the free sulfonic acids, the products are extremely readily soluble in water and, because of their highly acid reaction, are also unstable, especially when the basic radical denotes a furfurylamino radical. If such products are required in special cases, it is advantageous to pass an aqueous solution of any desired salt through a strongly acid ion exchanger in the $H^+$ form.

For therapeutic purposes, the alkali metal salts, which are readily soluble in water, give a neutral reaction, and are very stable, preferably the sodium or potassium salt, are preferably used and in general the sodium salts are more readily soluble in water than the potassium salts. For special purposes, calcium salts and magnesium salts can also be used under certain circumstances. Ammonium salts can also be therapeutically valuable.

Examples which may be mentioned of salts having a particularly good solubility in water are the diethanolammonium salt, the N,N,N-tris-hydroxymethylammonium salt and the glucose-ammonium salt. Much more frequently it is desired to reduce the solubility in water by forming a salt with specific bases, in order, where appropriate, to achieve a protracted action in the case of oral administration. Suitable amine components for such salts are, for example, dicyclohexylamine, N,N'-dibenzylethylenediamine, 2-aminothiazole, 2-aminothiazoline, xantinol and tetramisol.

Further salts of great pharmacological significance are the salts of the process products with basic potassium-retaining compounds, such as, for example, amiloride or triamterene, or with basic antihypertensive agents, such as, for example, clonidine, dihydralazine or guanethidine.

As tests on rats and dogs have shown, the novel products are excellent salidiuretic agents with a very rapid onset of action and a period of action of 4 to 10 hours. A particular advantage of the novel compounds is the advantageous sodium/potassium ratio.

The high solubility in water of the products and the neutral pH of the aqueous solutions are also highly advantageous for therapeutic use. The products are therefore ideally suitable in particular for intravenous administration. The products are reliably effective after oral administration also, in which case the action starts 1-2 hours after administration.

In human therapy, formulations which can be used are preferably aqueous injection solutions with a total content of 0.1 to 50 mg of the alkali metal salts, for intravenous administration, and tablets, dragees or capsules containing 1 to 200 mg of the active ingredient and the conventional fillers and excipients, for oral administration.

The invention is illustrated in more detail by the examples which follow. In addition to the end products described in the examples, the following compounds according to the invention can be prepared:

| R | Ar | Z |
|---|---|---|
| 3-Chlorophenyloxy | 2-Thienyl | K |
| 3-Tolyloxy | 2-Thienyl | K |
| 3-Bromophenoxy | 2-Furyl | K |
| 4-Bromophenoxy | 2-Furyl | K |
| 3-Bromophenoxy | 2-Thienyl | K |
| 3-Chlorophenylthio | 2-Furyl | Na |
| 3-Tolylthio | 2-Furyl | Na |
| 2-Tolylthio | 2-Furyl | Na |
| 3-Methoxyphenylthio | 2-Furyl | Na |

EXAMPLE 1

The sodium salt of N-(2-furylmethyl)-4-phenoxy-5-sulfamoyl-orthanilic acid (a) 45.4 g (0.1 mole) of p-cresyl 2-chloro-4-phenoxy-5-sulfamoylbenzenesulfonate and 150 ml of freshly distilled furfurylamine are stirred at 80° C. for one hour and the excess amine is then stripped off in vacuo. The evaporation residue is partitioned between 1.0 l of 10 percent strength acetic acid and 0.3 l of ethyl acetate and the organic phase is separated off and washed twice with 0.3 l of 5 percent strength acetic acid and twice with 0.3 l of water. The dried ethyl acetate solution is evaporated and p-cresyl N-(2-furylmethyl)-4-phenoxy-5-sulfamoyl-orthanilate is isolated from the residue by recrystallizing twice from ethanol.

10.5 g (20% of theory) of colorless crystals having a melting point of 175°-176° C.

(b) 5.2 g (10 mmoles) of p-cresyl N-(2-furylmethyl)-4-phenoxy-5-sulfamoyl-orthanilate and 50 ml of 2 N NaOH are heated under reflux for 2 hours. The pH of the clear reaction solution is then adjusted to 5 with 5 N HCl, at room temperature, and the p-cresol is removed by extracting by shaking with 50 ml of diisopropyl ether. After concentrating the aqueous solution to 30 ml and neutralizing with 2 N HCl, the end product crystallizes overnight at room temperature. It is dried at 60° C.

3.4 g (75% of theory) of colorless crystals having a decomposition point of 232° C.

Starting Material 101 g of triethylamine, dissolved in 1.0 l of tetrahydrofurane, are added dropwise in the course of one hour, at 5°-10° C., while stirring, to a solution of 344 g (1.0 mole) of 1,3-dichlorobenzene-4,6-disulfonyl dichloride and 108 g of p-cresol in 4.0 l of tetrahydrofurane. Ammonia gas is then passed in excess into the reaction mixture at 5°–10° C. Water is then added in an amount such that the ammonium chloride and triethylamine hydrochloride go into solution, the solution is neutralized with HCl and concentrated in vacuo to one third its volume, and 3 l of water are added to the concentrate. The crude product, which has precipitated as an amorphous substance, is separated by decanting the supernatant liquor and is dissolved in 1 l of ethanol with warming. After standing overnight at room temperature, the bis-p-cresyl 1,3-dichlorobenzene-4,6-disulfonate which has separated out as crystals (about 75 g, by-product!) is filtered off, 0.5 l of water is added in portions to the filtrate and the product is allowed to crystallize at room temperature for one day. After filtering off, it is dried on a steam bath.

245 g (62% of theory) of p-cresyl 2,4-dichloro-5-sulfamoylbenzenesulfonate having a melting point of 155°–157° C.

39.7 g (0.1 mole) of this ester are stirred with 11.3 g of phenol and 6.9 g of powdered potassium carbonate in 125 ml of dimethylformamide for 2 hours at 110° C. The solvent is then stripped off in vacuo and the residue is extracted twice with warm water. The undissolved crystalline constituent is filtered off and recrystallized from methanol. This gives 19.3 g (43% of theory) of o-cresyl 2-chloro-4-phenoxy-5-sulfamoylbenzenesulfonate having a melting point of 157°–159° C.

A further 8 g of the compound are obtained by evaporating the mother liquor and chromatographing the residue in a column of silica gel (300 g) soaked in toluene, using toluene/ethyl acetate (0 to 10% of ethyl acetate).

The other starting materials of the general formula III can be obtained in an analogous manner.

EXAMPLE 2

The sodium salt of N-(2-furylmethyl)-4-(4-tolyloxy)-5-sulfamoyl-orthanilic acid (a) 46.8 g (0.1 mole) of p-cresyl 2-chloro-4-(4-tolyloxy)-5-sulfamoyl-benzenesulfonate and 100 ml of furfurylamine are warmed at 80°–85° C. for one hour, while stirring, and the reaction solution is then worked up analogously to Example 1a. The amorphous crude product is introduced, as a solution in 100 ml of toluene, onto a column of 500 g of silica gel soaked in toluene, and eluted first with toluene and subsequently with the addition of ethyl acetate (continuous, rising to a maximum of 8%). The fractions corresponding to the main product are evaporated and the crystalline residue is ground with diisopropyl ether and filtered off. The product is dried at 80° C./0.1 mm Hg.

33 g (62% of theory) of p-cresyl N-(2-furylmethyl)-4-(4-tolyloxy)-5-sulfamoyl-orthanilate having a melting point of 136°–138° C.

(b) 5.3 g (19 mmoles) of the ester from (a) are warmed with 50 ml of 1 N NaOH for 30 minutes, while stirring, on a steam bath. The saponification product is isolated analogously to Example 1b and is recrystallized from 5 percent strength aqueous NaCl solution and dried at 60° C./0.1 mm Hg.

3.2 g (70% of theory) of colorless crystals which decompose above 236° C.

Starting Material

A mixture of 39.7 g (0.1 mole) of p-cresyl 2,4-dichloro-5-sulfamoylbenzenesulfonate, 120 ml of dimethylformamide, 6.9 g of powdered potassium carbonate and 10.8 g of p-cresol is stirred for one hour at 115° C. The dimethylformamide is then stripped off in vacuo, the evaporation residue is treated with 1 l of water and the amorphous precipitate is separated off and recrystallized from ethanol.

19.2 g (41% of theory) of p-cresyl 2-chloro-5-sulfamoyl-4-(4-tolyloxy)-benzenesulfonate having a melting point of 223°–225° C.

EXAMPLE 3

The sodium salt of N-(2-furylmethyl)-4-phenylthio-5-sulfamoyl-orthanilic acid (a) 47.0 g (0.1 mole) of p-cresyl 2-chloro-4-phenylthio-5-sulfamoylorthanilate and 120 ml of furfurylamine are stirred at 85° to 90° C. for 2 hours and the reaction solution is then stirred into 1.2 l of 10 percent strength acetic acid. The crude product, which has precipitated as crystals, is purified by recrystallization from ethanol.

41 g (89% of theory) of p-cresyl N-(2-furylmethyl)-4-phenylthio-5-sulfamoylorthanilate having a melting point of 151°–153° C.

(b) 5.3 g (10 mmoles) of the ester from (a) and 50 ml of 1 N NaOH are heated under reflux for 2 hours. After cooling to room temperature, the pH of the clear reaction solution is adjusted to 2 with 0.5 N HCl and the p-cresol is removed by extracting by shaking with 30 ml of diisopropyl ether. The end product crystallizes out of the aqueous phase, which has been separated, after neutralizing with 2 N NaOH, on standing overnight at room temperature. It is dried on a steam bath.

4.1 g (89% of theory) of colorless crystals which decompose above 236° C.

Starting Material 39.7 g (0.1 mole) of p-cresyl, 2,4-dichloro-5-sulfamoylbenzenesulfonate, 120 ml of dimethylformamide, 6.9 g of powdered potassium carbonate and 11.2 g of thiophenol are stirred for one hour at 100° C., the mixture is then stirred into 1.5 l of water and the resin which has precipitated is separated and recrystallized from ethanol.

20.5 g (44% of theory) of p-cresyl 2-chloro-4-phenylthio-5-sulfamoylorthanilate having a melting point of 199°–201° C.

EXAMPLE 4

The sodium salt of N-(2-thienylmethyl)-4-(4-tolyloxy)-5-sulfamoyl-orthanilic acid (a) 46.8 g (0.1 mole) of p-cresyl 2-chloro-5-sulfamoyl-4-(4-tolyloxy)-benzenesulfonate are dissolved in 75 ml of dimethylformamide and, after adding 55 g of thenylamine, the mixture is stirred at 90° C. for one hour. The reaction solution is then stirred into 1 l of 10 percent strength acetic acid and the crystalline precipitate is filtered off and, in the moist state in which it is obtained on the suction filter, recrystallized from methanol.

23.5 g (43% of theory) of p-cresyl N-(2-thienylmethyl)-4-(4-tolyloxy)-5-sulfamoyl-orthanilate having a melting point of 180°–181° C.

(b) 5.4 g (10 mmoles) of the ester from (a) are saponified analogously to Example 1(b) and the sodium salt is purified by recrystallization from water.

3.8 g (80% of theory) of colorless prisms having a melting point of 230° C. with decomposition.

EXAMPLE 5

The sodium salt of N-(2-furylmethyl)-4-methyl-5-sulfamoyl-orthanilic acid (a) 37.6 g (0.1 mole) of p-cresyl 2-chloro-4-methyl-5-sulfamoylbenzenesulfonate and 100 ml of furfurylamine are stirred at 90° C. under nitrogen for 2 hours and the reaction solution is then worked up analogously to Example 1(a). The amorphous crude product is recrystallized from toluene.

32 g (73% of theory) of p-cresyl N-(2-furylmethyl)-4-methyl-5-sulfamoyl-orthanilate having a melting point of 143°–144° C.

(b) 4.4 g (10 mmoles) of the ester from (a) are saponified analogously to Example 1(b) with NaOH and the sodium salt which has crystallized out from the aqueous solution is purified by recrystallization from ethanol.

2.8 g (75% of theory) of colorless crystals having a decomposition point of 235° C.

Starting Material 30.4 g (0.1 mole) of 2-chloro-4-methyl-5-sulfamoylbenzenesulfonyl chloride and 10.8 g of p-cresol are dissolved in 0.4 l of acetone and 10.1 g of triethylamine, dissolved in 50 ml of acetone, are added dropwise to the mixture at room temperature, while stirring. The acetone is then stripped off in vacuo, the residue is treated with water and the crystalline precipitate is filtered off and recrystallized from ethanol.

31 g of p-cresyl-2-chloro-4-methyl-5-sulfamoylbenzenesulfonate having a melting point of 157°–159° C.

EXAMPLE 6

The sodium salt of N-(2-thienylmethyl)-4-methyl-5-sulfamoyl-orthanilic acid (a) 37.6 g (0.1 mole) of p-cresyl 2-chloro-4-methyl-5-sulfamoylbenzenesulfonate and 75 ml of thenylamine are stirred at 90° C. under nitrogen for 3 hours and the reaction mixture is then introduced into 1 l of 10 percent strength acetic acid. The crude product, which has precipitated out as crystals, is purified by recrystallization from ethanol.

36 g (80% of theory) of p-cresyl N-(2-thienylmethyl)-4-methyl-5-sulfamoyl-orthanilate having a melting point of 163°–165° C.

(b) 4.5 g (10 mmoles) of the ester from (a) are saponified analogously to Example 1(b). After concentrating the aqueous-neutral solution, the sodium salt crystallizes at room temperature.

2.6 g (69% of theory) of slightly yellowish crystals having a melting point of 235° C. with decomposition.

EXAMPLE 7

The sodium salt of N-(2-thienylmethyl)-4-phenylthio-5-sulfamoyl-orthanilic acid (a) 47.0 g (0.1 mole) of p-cresyl 2-chloro-4-phenylthio-5-sulfamoylorthanilate are reacted analogously to Example 3(a) with 100 ml of 2-thenylamine and the condensation product is purified by recrystallization from methanol.

32 g (58% of theory) of p-cresyl N-(2-thienylmethyl)-4-phenylthio-5-sulfamoyl-orthanilate having a melting point of 153° C.

(b) Saponification of 5.5 g of the ester from (a) with NaOH, analogously to Example 3(b), gives 3.1 g (64% of theory) of the corresponding sodium sulfonate having a decomposition point of 214° C.

EXAMPLE 8

The potassium salt of N-(2-furylmethyl)-4-chloro-5-sulfamoyl-orthanilic acid A mixture of 16.3 g (50 mmoles) of 4-chloro-2-fluoro-5-sulfamoylbenzenesulfonic acid dihydrate, 50 ml of dioxane and 20 ml of furfurylamine is stirred for one hour at 85° C. and the dioxane is then stripped off in vacuo. The evaporation residue is dissolved in 100 ml of 2 N NaOH, the furfurylamine is removed from the solution by extracting three times by shaking with 100 ml portions of ethyl acetate and the solution is then neutralized with 5 N HCl and evaporated to dryness. The evaporation residue, which has been dried at 100° C., is extracted twice with 0.2 l portions of boiling ethanol. The end product crystallizes out of the combined ethanol solutions, which have been concentrated to half their volume, overnight at room temperature.

15.7 g (81% of theory); decomposition point 265° C.

Starting Material 185 g of phosphorus oxychloride are added in portions to a solution of 210 g (1.0 mole) of 2-chloro-4-fluorobenzenesulfonamide in 0.6 l of dimethylformamide, at room temperature, whilst stirring, and the mixture is then warmed at 90°–95° C. for 2 hours, while stirring, and subsequently stirred into 3 l of water. The condensation product, which has precipitated as crystals, is filtered off, washed with water and dried on a steam bath.

230 g (87% of theory) of 2-chloro-4-fluoro-N-dimethylaminomethylidene-benzenesulfonamide having a melting point of 127°–129° C.

84 ml of fuming nitric acid are allowed to run into 0.8 l of 20 percent strength oleum at 20°–30° C. and 265 g of the above sulfonamide derivative are then introduced in portions. The mixture is stirred at 55° C. for 2 hours and then added dropwise to 5 kg of ice. The nitro compound, which has precipitated as crystals, is filtered off, washed well with water and dried at 60° C.

290 g (94% of theory) of 4-chloro-5-dimethylaminomethylidene-sulfamoyl-2-fluoro-nitrobenzene having a melting point of 164°–165° C.

155 g (0.5 mole) of the above nitro compound are dissolved in 3.0 l of tetrahydrofurane and hydrogenated in a shaking duck in the presence of palladium black. After 34 l of $H_2$ have been taken up, the hydrogenation ceases. The catalyst is separated off, the solution is evaporated and the residue is ground at room temperature with ethanol, whereupon the amino compound crystallizes in the form of colorless platelets. After filtering off, the product is recrystallized from nitromethane.

125 g (90% of theory) of 4-chloro-5-dimethylaminomethylidene-sulfamoyl-2-fluoro-aniline having a melting point of 202°–205° C.

56 g (0.2 mole) of the amino compound are stirred with a mixture of 0.4 l of 2 N NaOH and 0.2 l of methanol at 40°–45° C. until a clear solution has formed and this solution is left to stand overnight at room temperature. The pH is then adjusted to 5 with HCl and the sulfonamide, which has precipitated as crystals, is filtered off, washed with water and dried on a steam bath.

41 g (91% of theory) of 4-chloro-2-fluoro-5-sulfamoylaniline having a melting point of 176°–179° C.

56 g (0.25 mole) of the aminosulfonamide are dissolved in a mixture of 0.1 l of concentrated HCl and 0.1 l of glacial acetic acid and the mixture is diluted with 0.1 l of water. A solution of 20 g of sodium nitrite in 0.1 l of water is then added dropwise at $-3°$ to $0°$ C., while stirring, the mixture is stirred for a further 4 minutes at $0°$ C. and the diazo solution is then introduced into a mixture, which has been prepared a short time previously, of 0.6 l of $SO_2$-saturated glacial acetic acid and 15 g of CuCl dihydrate in 50 ml of water, while stirring. After the evolution of nitrogen has ceased, the mixture is diluted with an equal volume of water and the crystalline precipitate is filtered off, washed well with water and dried in air.

48 g (62% of theory) of 4-chloro-2-fluoro-5-sulfamoylbenzenesulfonyl chloride having a melting point of 170°–172° C.

31 g (0.1 mole) of the sulfonyl chloride are stirred with 1 l of water for 30 minutes on a steam bath and the clear reaction solution is then evaporated in vacuo. The product, which initially is amorphous, crystallizes completely, radiating outwards, at room temperature.

30 g (92% of theory) of 4-chloro-2-fluoro-5-sulfamoylbenzenesulfonic acid dihydrate.

EXAMPLE 9

The potassium salt of
N-(2-furylmethyl)-5-sulfamoyl-4-(3-tolyloxy)orthanilic acid 32.6 g (0.1 mole) of 4-chloro-2-fluoro-5-sulfamoylbenzenesulfonic acid dihydrate, 100 ml of dioxane and 45 g of 2-thienylmethylamine are warmed at 85° C. for half an hour, while stirring, and the dioxane is then stripped off in vacuo. The evaporation residue is taken up in 0.4 l of water and the pH of the filtered solution is adjusted to 7.5 with 5 N HCl. The end product starts to crystallize after grinding and is filtered off after standing for 4 hours at room temperature.

25 g (50% of theory) of colorless crystals having a melting point of 202°–204° C.

EXAMPLE 10

The sodium salt of
N-(2-furylmethyl)-4-(4-methoxyphenoxy)-5-sulfamoyl-orthanilic acid (a) 48.4 g (0.1 mole) of p-cresyl 2-chloro-4-(4-methoxyphenoxy)-5-sulfamoylbenzenesulfonate are reacted with 100 ml of furfurylamine, and the product is worked up and purified, analogously to Example 2a.

12 g (22% of theory) of p-cresyl N-(2-furylmethyl)-4-(4-methoxyphenoxy)-5-sulfamoyl-benzenesulfonate having a melting point of 117°–120° C.

(b) 5.4 g (10 mmoles) of the ester from (a) and 50 ml of 1 N NaOH are warmed for one hour, while stirring, on a steam bath. The saponification product is isolated analogously to Example 1b.

4.2 g (88% of theory) of colorless crystals which decompose above 225° C.

Starting Material

A mixture of 39.7 g (0.1 mole) of p-cresyl 2,4-dichloro-5-sulfamoylbenzenesulfonate, 120 ml of dimethylformamide, 6.9 g of powdered potassium carbonate and 12.4 g of 4-hydroxyanisole is stirred for one hour at 115° C. The dimethylformamide is then stripped off in vacuo, the evaporation residue is treated with 1 l of water and the product is filtered off and washed with water and hot ethanol.

25.3 g (52% of theory) of p-cresyl 2-chloro-4-(4-methoxyphenoxy)-5-sulfamoylbenzenesulfonate having a melting point of 198°–200° C.

EXAMPLE 11

The potassium salt of
N-(2-furylmethyl)-4-phenoxy-5-sulfamoyl-orthanilic acid (a) 44.0 g (0.1 mole) of phenyl 2-chloro-4-phenoxy-5-sulfamoylbenzenesulfonate having a melting point of 180°–181° C. (from methanol) are stirred with 30 ml of furfurylamine and 100 ml of dimethylformamide for 2 hours at 90° C. and the reaction solution is then evaporated in vacuo. The evaporation residue is boiled up with 0.5 l of water and the undissolved constituent is separated by decanting the supernatant liquor and is recrystallized from 0.25 l of methanol.

16.0 g (32% of theory) of phenyl N-(2-furylmethyl)-4-phenoxy-5-sulfamoylorthanilate having a melting point of 176°–178° C.

(b) 12.5 g (25 mmoles) of the above ester and 125 ml of 1 N KOH are boiled under reflux for 1.5 hours. After the clear reaction solution has cooled to room temperature and after neutralizing with 2 N HCl, the end product rapidly crystallizes out. After standing for one hour at $+10°$ C., the product is filtered off, washed with ice-water and diethyl ether and dried on a steam bath.

9.7 g (84% of theory) of colorless platelets having a decomposition point of 217° C.

EXAMPLE 12

The potassium salt of
N-(2-furylmethyl)-5-sulfamoyl-4-(3-tolyloxy)-orthanilic acid (a) 10.3 g (22 mmoles) of p-cresyl 2-chloro-5-sulfamoyl-4-(3-tolyloxy)-benzenesulfonate and 25 ml of furfurylamine are warmed at 60° C. for 2 hours, whilst stirring, and the reaction mixture is worked up analogously to Example 2a. This gives 1.3 g of p-cresyl N-(2-furylmethyl)-5-sulfamoyl-4-(3-tolyloxy)-orthanilate having a melting point of 131°–133° C.

(b) The entire ester from (a) is stirred with 40 ml of 2 N KOH for 2 hours at 95° C. and the pH of the saponification solution is adjusted to 6 with 5 N HCl at room temperature. The end product crystallizes immediately. After standing for one hour at room temperature, the product is filtered off and washed with a little ice-water and the colorless product is dried on a steam bath.

1.0 g (85% of theory); decomposition point 218° C.

EXAMPLE 13

The potassium salt of
N-(2-furylmethyl)-4-(3-methoxyphenoxy)-5-sulfamoyl-orthanilic acid (a) 4.4 g (9 mmoles) of p-cresyl 2-chloro-4-(3-methoxyphenoxy)-5-sulfamoylbenzenesulfonate having a melting point of 155° C. are stirred with 20 ml of furfurylamine for 2 hours at 80°–85° C. and the reaction mixture is worked up analogously to Example 2a. After evaporating those fractions obtained from column chromatography which correspond to the main product, p-cresyl N-(2-furylmethyl)-4-(3-methoxyphenoxy)-5-sulfamoyl-orthanilate is obtained in an amorphous form. The substance is a single compound according to chromatography. The NMR spectrum (in DMSO) corresponds to the structure.

3.0 g (61% of theory) of colorless resin; thin layer chromatography (silica gel) using chloroform/methanol (10:1) as the solvent: Rf 0.75.

(b) 3.0 g of the ester from (a) are stirred with 40 ml of 2 N KOH for 2 hours at 95° C. and the clear reaction solution is then neutralized at room temperature with 2 N HCl and concentrated to 40 ml in vacuo. After standing for two days at +5° C., the end product, which has precipitated as crystals, is filtered off, washed with a little ice-water and dried on a steam bath.

0.8 g (29% of theory) of colorless crystals having a decomposition point of 200° C.

EXAMPLE 14

The potassium salt of N-(2-thienylmethyl)-4-phenoxy-5-sulfamoyl-orthanilic acid (a) 3.2 g (8 mmoles) of phenyl 2-chloro-4-phenoxy-5-sulfamoylbenzenesulfonate and 5.6 g of 2-thenylamine are warmed at 90° C. for 2 hours, while stirring. The reaction solution is introduced into 0.2 l of 5 percent strength acetic acid and the reaction product, which has precipitated in an amorphous form, is separated by decanting the supernatant liquor.

The crude product is crystallized from 30 ml of methanol as colorless prisms.

2.1 g (51% of theory) of phenyl N-(2-thienylmethyl)-4-phenoxy-5-sulfamoyl-orthanilate having a melting point of 181°-183° C.

(b) 1.9 g of the above ester are stirred with 15 ml of 2 N KOH for 4 hours at 95° C. The pH of the clear reaction solution is adjusted to 6 at room temperature with 5 N HCl. The end product crystallizes out of the solution, which at first is still clear, after grinding with a glass rod. After washing with water, the product is dried on a steam bath.

1.1 g (62% of theory) of colorless platelets having a decomposition point of 248° C.

EXAMPLE 15

The sodium salt of N-(2-furylmethyl)-4-(4-methoxyphenylthio)-5-sulfamoyl-orthanilic acid (a) 10.0 g of p-cresyl 2-chloro-4-(4-methoxyphenylthio)-5-sulfamoyl-orthanilate having a melting point of 188°-190° C. are stirred with 25 ml of furfurylamine for 1.5 hours at 70° C. The p-cresyl N-(2-furylmethyl)-4-(4-methoxyphenylthio)-5-sulfamoyl-orthanilate which has precipitated as crystals when the reaction solution is introduced into 0.3 l of 10 percent strength acetic acid is washed thoroughly, on the suction filter, with water and then boiled with 100 ml of ethanol and filtered off at room temperature.

6.3 g (56% of theory) of yellowish crystals having a melting point of 159°-161° C.

(b) 5.6 g (10 mmoles) of the above ester are stirred with 50 ml of 1 N KOH for one hour on a steam bath and the pH of the reaction solution is then adjusted to 7 at room temperature with 2N HCl. The end product crystallizes immediately. After washing with water and ethanol, it is dried on a steam bath.

5.0 g (98% of theory); decomposition point 205° C.

EXAMPLE 16

The sodiUm salt of N-(2-furylmethyl)-4-(4-tolylthio)-5-sulfamoyl-orthanilic acid (a) 14.4 g (30 mmoles) of p-cresyl 2-chloro-5-sulfamoyl-4-(4-tolylthio)-orthanilate having a melting point of 181°-183° C. are reacted, analogously to Example 15 a, with 35 ml of furfurylamine and the p-cresyl N-(2-furylmethyl)-5-sulfamoyl-4-(4-tolylthio)-orthanilate precipitated as crystals by dilute acetic acid is purified by recrystallization from 0.3 l of ethanol.

10.0 g (61% of theory) of yellowish crystals having a melting point of 169°-171° C.

(b) 9.8 g (18 mmoles) of the above ester are saponified by heating for one hour with 100 ml of 1 N NaOH on a steam bath. The end product, which has been precipitated as crystals by neutralizing with 5 N HCl at room temperature, is filtered off, after standing for a short time at room temperature, washed with water and diisopropyl ether and dried on a steam bath.

5.6 g (65% of theory); decomposition point 233° C.

EXAMPLE 17

The potassium salt of N-(2-furylmethyl)-4-(4-chlorophenylthio)-5-sulfamoyl-orthanilic acid (a) 10.1 g (20 mmoles) of p-cresyl 2-chloro-4-(4-chlorophenylthio)-5-sulfamoyl-orthanilate having a melting point of 189° C. are reacted, analogously to Example 15A, with 25 ml of furfurylamine, and the p-cresyl 4-(4-chlorophenylthio)-N-(2-furylmethyl)-5-sulfamoyl-orthanilate precipitated as crystals by dilute acetic acid is recrystallized from 02. l of ethanol.

7.6 g (67% of theory); melting point 152° C.

(b) 7.4 g (13 mmoles) of the above ester are stirred with a mixture of 65 ml of 1 N KOH and 15 ml of dioxane for 1 hour at 95° C. and the reaction solution is then neutralized at room temperature with 2 N HCl. The end product crystallizes immediately. After standing for one hour at room temperature, it is filtered off, washed with water and ethanol and dried on a steam bath.

6.1 g (91% of theory); decomposition point 233° C.

EXAMPLE 18

The potassium salt of N-(2-furylmethyl)-4-(3-chlorophenoxy)-5-sulfamoyl-orthanilic acid (a) 8.0 g (16.5 mmoles) of p-cresyl 2-chloro-4-(3-chlorophenoxy)-5-sulfamoyl-orthanilate are stirred with 4.9 g of furfurylamine and 20 ml of dimethylformamide for 2 hours at 90° C. The crude product, which has precipitated in an amorphous form on introducing the reaction solution into 0.3 l of 10 percent strength acetic acid, is chromatographed on a column of 100 g of silica gel in toluene/ethyl acetate (maximum 5% of ethyl acetate) and the main fraction (Rf 0.75, thin layer chromatography on silica gel in chloroform/methanol, 10:1, as the solvent; the by-products without exception have lower Rf values) is recrystallized from diisopropyl ether.

1.2 g (13% of theory); melting point 151°-153° C.

(b) All of the p-cresyl 4-(3-chlorophenoxy)-N-(2-furylmethyl)-5-sulfamoyl-orthanilate from (a) is warmed with 20 ml of 2 N KOH for 15 minutes on a steam bath and the reaction solution is then neutralized at room temperature with 2 N HCl. The end product, which has precipitated as crystals, is filtered off after standing for a short time at room temperature and is washed with water and dried on a steam bath.

0.9 g (83% of theory) of colorless crystals which decompose above 250° C.

EXAMPLE 19

The potassium salt of N-(2-furylmethyl)-4-(4-chlorophenoxy)-5-sulfamoylorthanilic acid is obtained analogously to Example 18, by saponifying the corresponding p-cresyl sulfonate (melting point 126°-128° C. after recrystallization from isopropanol) with 2 N KOH (4 hours on a steam bath).

Yield: 0.8 g (73% of theory); decomposition point 220° C.

We claim:

1. A compound of the formula

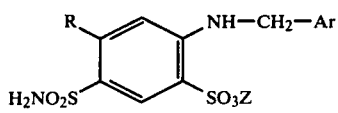

wherein
Ar is furyl;
R is phenoxy, phenylthio, or phenoxy or phenylthio substituted by a chlorine or bromine atom or by methyl or methoxy, and
Z is hydrogen or a physiologically acceptable metal ion, ammonium ion, or substituted ammonium ion.

2. A compound as in claim 1 wherein Z is an alkali metal ion.

3. A compound as in claim 1 wherein R is phenoxy or phenylthio, Ar is 2-furyl, and Z is sodium or potassium.

4. A compound as in claim 1 which is N-(2-furylmethyl)-4-phenoxy-5-sulfamoyl-orthanilic acid or the sodium salt or potassium salt thereof.

5. A compound as in claim 1 which is N-(2-furylmethyl)-4-phenylthio-5-sulfamoyl-orthanilic acid or the sodium salt thereof.

6. A compound as in claim 1 which is N-(2-furylmethyl)-4-(3-tolyloxy)-5-sulfamoyl-orthanilic acid or the potassium salt thereof.

7. A compound as in claim 1 which is N-(2-furylmethyl)-4-(4-chlorophenoxy)-5-sulfamoyl-orthanilic acid or the potassium salt thereof.

8. A diuretically and saluretically active pharmaceutical composition comprising 0.1 to 200 mg, of a compound as in claim 1 per dosage unit, and a pharmaceutically tolerable carrier therefor.

9. A method of inducing diuresis or saluresis in a patient which comprises administering to said patient a diuretically or saluretically effective amount of a compound as in claim 1.